United States Patent
Godbole et al.

(10) Patent No.: US 7,071,348 B2
(45) Date of Patent: Jul. 4, 2006

(54) PROCESS FOR THE PURIFICATION OF OLEFINICALLY UNSATURATED NITRILES

(75) Inventors: Sanjay P. Godbole, Solon, OH (US); Milind V. Kantak, Mayfield Hts., OH (US); Oliver M. Wahnschafft, Winchester, MA (US)

(73) Assignee: The Standard Oil Company, Warrenville, IL (US)

( * ) Notice: Subject to any disclaimer, the term of this patent is extended or adjusted under 35 U.S.C. 154(b) by 0 days.

(21) Appl. No.: 11/031,277

(22) Filed: Jan. 6, 2005

(65) Prior Publication Data

US 2005/0187401 A1    Aug. 25, 2005

Related U.S. Application Data

(60) Provisional application No. 60/535,414, filed on Jan. 9, 2004.

(51) Int. Cl.
  *C07C 255/03* (2006.01)
(52) U.S. Cl. .................................................. 558/463
(58) Field of Classification Search ................. 558/468
  See application file for complete search history.

(56) References Cited

U.S. PATENT DOCUMENTS 3,399,120 A * 8/1968 Lovett .......................... 203/84

* cited by examiner

*Primary Examiner*—Taofiq Solola
*Assistant Examiner*—Ebenezer Sackey
(74) *Attorney, Agent, or Firm*—David P. Yusko

(57) ABSTRACT

A process for the recovery and purification of olefinically unsaturated nitrites from a process stream produced by the ammoxidation of a hydrocarbon feedstock comprising contacting the process stream comprising olefinically unsaturated nitrile with an aqueous quench liquid in a quench apparatus to produce a gaseous quench effluent comprising olefinically unsaturated nitrile; contacting the gaseous quench effluent with a liquid comprising water in an absorber apparatus to form an aqueous mixture comprising absorbed olefinically unsaturated nitrile; withdrawing from the absorber apparatus a side-draw stream comprising water and a bottoms stream comprising olefinically unsaturated nitrile; introducing the bottoms stream to a first distillation column where the bottoms stream is distilled in an extractive distillation to form a top fraction comprising olefinically unsaturated nitrile, and directing the side-draw stream comprising water to the upper portion of the first distillation column to assist with the extractive distillation of the olefinically unsaturated nitrile in the first distillation column.

16 Claims, 1 Drawing Sheet

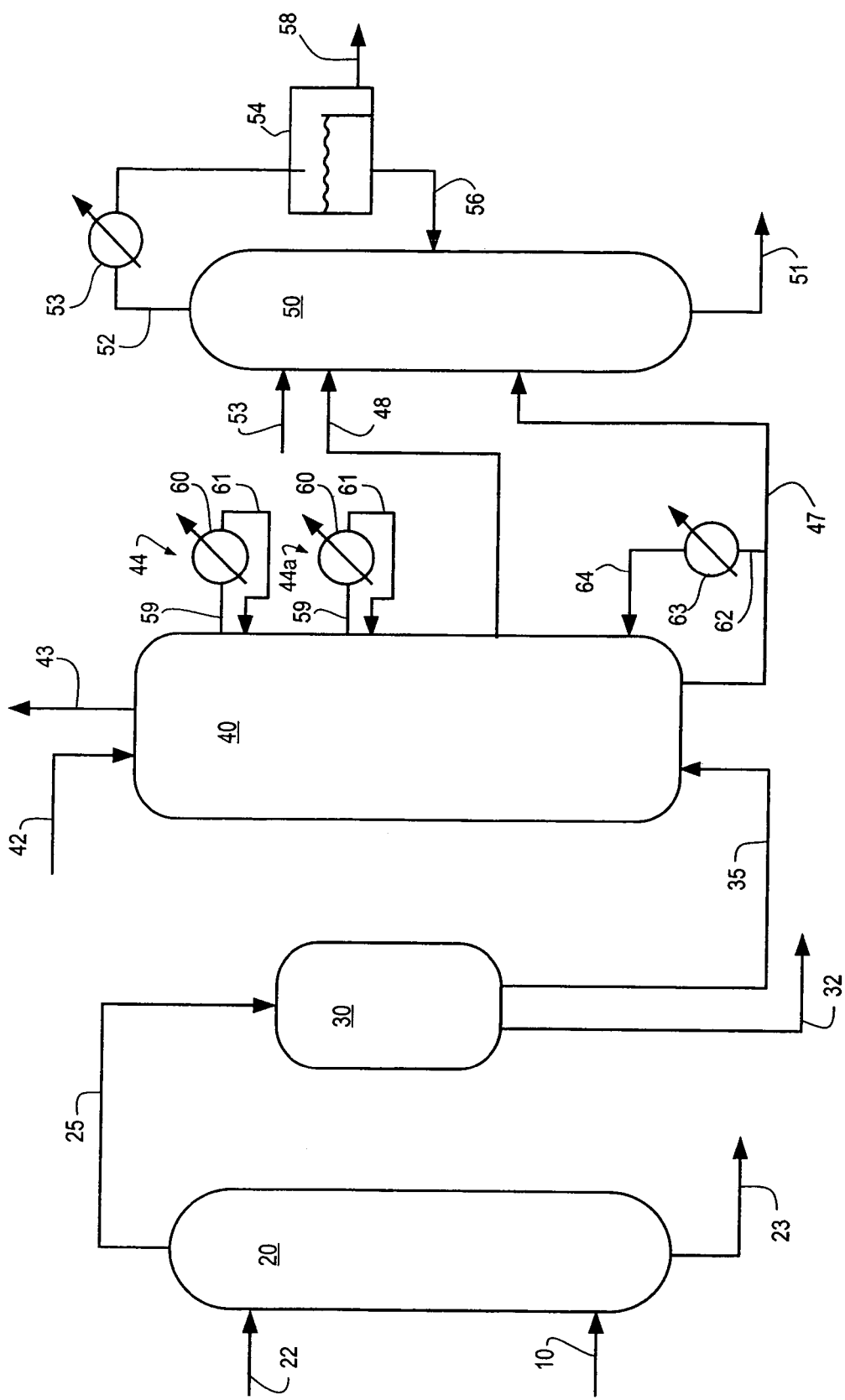

PROCESS FOR THE PURIFICATION OF OLEFINICALLY UNSATURATED NITRILES

This application claims the benefit of U.S. Provisional Patent Application 60/535,414 filed on Jan. 9, 2004.

BACKGROUND OF THE INVENTION

Acrylonitrile is an important commodity chemical used mainly as monomer for the manufacture of a wide variety of polymeric materials such as polymers for acrylic fibers used in textiles, and in resins such as ABS and SAN resins. Worldwide, acrylonitrile is produced in amounts exceeding four million metric tons per year. The most commonly used process for manufacturing acrylonitrile or other olefinically unsaturated nitrile, such as methacrylonitrile, is to react a suitable hydrocarbon, such as propylene or propane for the manufacture of acrylonitrile, or isobutylene for the manufacture of methacrylonitrile, in an ammoxidation reactor in the presence of ammonia using air or other source of molecular oxygen as an oxidant. Such oxidation reactions, also called ammoxidation reactions, typically use a solid, particulate, heterogeneous catalyst in a fluidized catalyst bed to catalyze the ammoxidation reaction and provide the desired acrylonitrile or methacrylonitrile in acceptable conversion and yield. In addition to producing an olefinically unsaturated nitrile, such ammoxidation reactions also generally produce other products such as acetonitrile, hydrogen cyanide (HCN) and other co-products. Processes for the catalytic ammoxidation of a hydrocarbon feed to acrylonitrile are disclosed, for example, in U.S. Pat. Nos. 4,503,001; 4,767,878; 4,863,891 and 5,093,299, all of which are incorporated herein by reference.

The processes widely used in commercial practice for recovering the products of such hydrocarbon ammoxidation, such as the ammoxidation of propylene to form acrylonitrile, generally comprise the steps of: a) contacting the effluent from an ammoxidation reactor in a quench tower with an aqueous quench liquid to cool the gaseous effluent; b) contacting the quenched gaseous effluent with water in an absorber, forming an aqueous solution comprising the ammoxidation products; c) subjecting the aqueous solution to a water extractive distillation in a distillation column, and d) removing a first overhead vapor stream comprising the unsaturated nitrile and some water from the top of the column, and collecting a liquid waste stream containing water and contaminants from the bottom of the column. Further purification of the olefinically unsaturated nitrile, such as acrylonitrile, may be accomplished by passing the overhead vapor stream to a second distillation column to remove at least some impurities from the acrylonitrile, and further distilling the partially purified acrylonitrile. The effluent from the ammoxidation reactor generally contains a certain amount of ammonia. Therefore, the quench liquid used in the quench tower may also contain a strong mineral acid, such as sulfuric acid, to react with and thereby form a water soluble salt of ammonia, such as ammonium sulfate. The used or spent quench fluid containing the ammonium sulfate and other components is typically treated or disposed of in an environmentally safe manner.

Recovery and purification systems for acrylonitrile and methacrylonitrile obtained by the ammoxidation of propylene, propane or isobutylene are disclosed, for example, in U.S. Pat. Nos. 3,399,120 and 3,936,360, all of which are incorporated herein by reference.

As mentioned above, the gaseous reactor effluent from an ammoxidation reactor during the manufacture of acrylonitrile is typically first directly contacted with a quenching liquid, typically water, in a quench apparatus such as a quench tower, to cool the effluent and remove a substantial amount of contaminants, such as polymeric materials, produced during the reaction. The cooled gaseous effluent from the quench apparatus is typically sent to an absorber apparatus, such as a wash column or absorber column, wherein the gaseous effluent is contacted with water. The liquid stream from the bottom of the absorber apparatus containing various nitriles, water and some impurities is then typically sent to a distillation column, also known as recovery column. In this distillation column, solvent water is used to extractively distill the stream from the absorber bottoms to produce an overhead vapor stream rich in acrylonitrile. As described in U.S. Pat. No. 3,399,120, for the recovery of acrylonitrile, the bottoms of the recovery column may be sent to a second distillation column, referred to as a stripping column. The overhead of the stripping column contains acetonitrile with a minor amount of water, and the liquid bottoms stream contains water and impurities. An alternate method of recovery of acrylonitrile, also found in U.S. Pat. No. 3,399,120, uses a side-draw from the extractive distillation column. This side-draw stream containing mostly acetonitrile and water is sent to a smaller stripping column where acetonitrile is removed overhead and the liquid bottoms containing mostly water is returned to the recovery column. When this method of recovery is used, the liquid bottoms stream from the recovery column is mostly water and impurities with traces of acetonitrile.

In the processes for the recovery of acrylonitrile just described, the absorber can be cooled at appropriate locations to facilitate the absorption of acrylonitrile in the scrubbing liquid so that the concentration of acrylonitrile in the process stream directed to the recovery column is maximized. An optimum lean water-to-acrylonitrile feed ratio is also maintained to maximize the product recovery in the absorber column. By lean water we mean a source of water that has a low level of organic components and is usually an aqueous stream obtained from a convenient source within the acrylonitrile recovery process. U.S. Pat. Nos. 3,044,966; 3,198,750; 3,352,764; 3,885,928 and 4,234,501, all of which are incorporated by reference herein, also disclose processes for the recovery and purification of acrylonitrile and methacrylonitrile from the ammoxidation of a hydrocarbon feed.

As described above, in the prior processes for the recovery and purification of acrylonitrile it is advantageous to add solvent water to the recovery column, preferably to the top or upper portion of the column to cause the extractive distillation of acrylonitrile and thereby produce an overhead stream rich in acrylonitrile with low levels of acetonitrile. This acrylonitrile-rich stream is typically purified by subsequent distillation process steps as mentioned above.

While the addition of water to the top of the recovery column during the recovery and purification of acrylonitrile results in the formation of the acrylonitrile-rich and HCN-rich overhead stream containing very low levels of acetonitrile, the added water increases the liquid volume to be handled by the column, and reduces the hydraulic capacity of the recovery column for processing the acrylonitrile-containing stream. The addition of such water also causes an energy inefficient separation. Thus, it would be desirable to have a process where the addition of extra water to the recovery column can be reduced or eliminated while maintaining recovery column separation efficiency. Such a process would provide for the processing of a greater feed throughput in an existing recovery column, thereby increasing the capacity of an existing manufacturing plant or, alternatively, allowing for the use of a smaller recovery column for the same amount of feed to be processed. The present invention provides such a process.

SUMMARY OF THE INVENTION

This invention is a process for the recovery and purification of olefinically unsaturated nitrites such as, acrylonitrile or methacrylonitrile, from a process stream produced by, for example, the ammoxidation reaction of a hydrocarbon feedstock, such as propylene, propane or isobutylene, in the presence of molecular oxygen, ammonia and an ammoxidation catalysts, comprising:

(a) contacting a process stream comprising an olefinically unsaturated nitrile with an aqueous quench liquid in a quench apparatus to produce a quench effluent;

b) contacting the quench effluent with a liquid comprising water in an absorber apparatus to form an aqueous mixture comprising absorbed olefinically unsaturated nitrile;

(c) withdrawing from the absorber apparatus a side-draw stream comprising water and a stream, preferably a bottoms stream, comprising olefinically unsaturated nitrile;

(d) introducing the stream comprising olefinically unsaturated nitrile to a first distillation column where the stream comprising olefinically unsaturated nitrile is distilled to form an upper, preferably top fraction comprising olefinically unsaturated nitrile, and (e) directing at least part of the side-draw stream comprising water to the upper portion of the first distillation column, preferably at a point above where the stream comprising olefinically unsaturated nitrile enters the first distillation column, and using the side-draw stream or at least part thereof for the extractive distillation of the olefinically unsaturated nitrile in the first distillation column.

BRIEF DESCRIPTION OF THE DRAWINGS

The FIGURE is a schematic representation of an embodiment of the present invention as applied to the recovery and purification of acrylonitrile.

DETAILED DESCRIPTION OF THE INVENTION

This invention will be described with respect to the recovery and purification of acrylonitrile produced by ammoxidation of propylene feed or feed comprising propylene. However, it is to be understood that this invention is not limited to the recovery and purification of acrylonitrile. This invention also includes the recovery and purification of olefinically unsaturated nitriles prepared from other suitable processes and other hydrocarbon feedstock such as, for example, acrylonitrile produced by the ammoxidation of propane or methacrylonitrile produced by the ammoxidation of isobutylene.

Any ammoxidation catalyst can be used to prepare process streams useful in the process of this invention where the hydrocarbon feed (e.g. propylene), source of molecular oxygen and ammonia are reacted in the presence of a suitable ammoxidation catalyst in a suitable reactor apparatus. For example, typical ammoxidation catalysts can be generalized by the following two formulae:

$A_aB_bC_cD_dMo_{12}O_x$ where

A=Li, Na, K, Cs, Tl and combinations thereof, preferably Cs and K
B=Ni, Co, Mn, Mg, Ca and combinations thereof, preferably Ni, Co and Mg
C=Fe, Cr, Ce, Cu, V, Sb, W, Sn, Ga, Ge, In, P and combinations thereof, preferably Fe, Cr and Ce
D=Bi and/or Te, preferably Bi
  a=0.1–4.0, preferably 0.1 to 0.5, especially preferred being 0.1 to 0.2
  b=0.1–10.0, preferably 5 to 9, especially preferred being 6 to 8, and
  c,d=0.1–10.0, preferably 0.5 to 4, especially preferred being 0.5 to 3; and

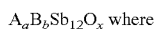

$A_aB_bSb_{12}O_x$ where

A=Fe, Cr, Ce, V, U, Sn, Ti, Nb and combinations thereof, preferably Fe, V, Sn and Ti
B=Mo, W, Co, Cu, Te, Bi, Zn, B, Ni, Ca, Ta and combinations thereof, preferably Mo and Cu
  a=0.1–16, preferably 2 to 12, especially preferred being 4 to 10
  b=0.0–12, preferably 1 to 10, especially preferred being 2 to 6, and
the value of x depends on the oxidation state of the elements used.

The suitable ammoxidation catalysts can be used either unsupported, or can be supported with silica, alumina, titania, zirconia and the like; however, silica is the preferred support. Catalysts and ammoxidation processes suitable for the ammoxidation of a hydrocarbon feed for preparing an olefinically unsaturated nitrile are disclosed, for example, in U.S. Pat. Nos. 3,642,930; 3,911,089; 4,485,079; 4,873,215; 5,093,299; 5,134,105 and 5,235,086, herein incorporated by reference.

Any source of oxygen, such as pure molecular oxygen, may be used. Air, however, is the preferred source of molecular oxygen. The molar ratio of molecular oxygen to the hydrocarbon feed to the reaction apparatus used for the ammoxidation reaction may be in the range of about 0.2:1 to about 3.0, and a ratio of about 1.5 to about 2.5 is preferred.

The molar ratio of ammonia to hydrocarbon fed to the reaction apparatus used for the ammoxidation reaction may vary between about 0.5:1 to about 5:1, preferably about 0.9:1 to about 1.3:1. Although there is no upper limit for the molar ratio of ammonia to hydrocarbon in the feed to the ammoxidation reactor, a ratio of up to about 1.3:1 is suitable.

In some cases water in the mixture fed to the reaction apparatus improves the selectivity of the reaction and yield of desired olefinically unsaturated nitrile.

In general, the molar ratio of added water to hydrocarbon feed, such as propylene, when water is added, is above about 0.25:1. Ratios on the order of 1:1 to 4:1 are particularly desirable, but higher ratios may be employed, for example, up to about 10:1.

The ammoxidation reaction is generally carried out at a temperature within the range of about 300 to about 600° C. The preferred temperature range is about 380 to about 500° C., especially preferred being about 400 to about 480° C.

The ammoxidation reaction may be carried out at any suitable pressure, however, preferably it is carried out at about atmospheric or above atmospheric pressure, for example, at about 1.5 to about 4 atmospheres gauge.

Contact times in the range of about 0.1 to about 50 seconds may be employed. In general, a contact time of about 1 to about 15 seconds is preferred.

Generally any apparatus of the type suitable for carrying out an ammoxidation reaction in the vapor phase may be used. The ammoxidation reaction may be conducted either continuously or intermittently. The catalyst bed may be a fixed-bed employing a large particulate or pelleted catalyst or, preferably, a so-called "fluidized" bed of catalyst may be employed.

The reactor effluent gas from the ammoxidation of the hydrocarbon feed, such as propylene, usually at a temperature between 370 and 485° C., is typically first passed to a quench system which is typically a tower with a countercurrent quench fluid flow. The purpose of the quench system is to remove excess ammonia, polymers and heavier impurities produced by the ammoxidation reaction, and to cool the reactor effluent gas. Typically water, usually containing sulfuric acid, is used as a quench liquid and is added to the upper part of the quench tower. The reactor effluent gas leaves the quench tower from the upper portion or top of the tower, typically at a temperature of about 30 to about 110° C. A bottom stream containing water, acid, polymers and other impurities is removed from the quench system.

After being cooled and treated in the quench system, the ammoxidation reactor effluent gases are typically sent to an absorber apparatus such as a wash column or absorber column. For example, the absorber can be a suitable column having one or more of trays, packing, or spray bars, and typically without reflux. Here, the effluent gases are typically contacted with water where the water is used for absorption. The water absorbs acrylonitrile, acetonitrile and some impurities to form an aqueous solution. The amount of water used is typically about 8 to about 18 parts of water by weight, preferably about 11 to about 15, and more preferably about 11 to about 13 to each part by weight of acrylonitrile in the quench effluent added to the absorber. The resulting aqueous solution containing the ammoxidation reaction products is removed from, typically, the bottom of the absorber. Non-absorbed gases are removed as a vapor stream typically from the top of the absorber. The aqueous solution from the absorber is directed to further processing to recover acrylonitrile and acetonitrile. Although this invention is not limited thereby, this further processing can be accomplished in accordance with the following procedures.

In one procedure, the aqueous solution is sent to an extractive distillation column or, so-called, recovery column. This recovery column may contain about 60 to about 120 trays. Heat is typically applied to the bottom of the column, usually by an indirect heat exchanger. Acrylonitrile and HCN are recovered as a vapor stream typically from the top of the recovery column and this stream is processed further to separate acrylonitrile from the HCN. Acetonitrile, water and impurities are removed from the bottom of the recovery column and can be passed to a stripper column, typically having about 20 to about 40 trays, such as, for example, 30 trays. In the stripper column, steam is suitably used to distill and separate the acetonitrile product from water. Acetonitrile is removed as an overhead vapor stream. A bottom stream containing water and impurities is removed from the stripper and may, for example, be recycled back to the quench column as quench liquid.

A another procedure of purifying the aqueous solution from the absorber apparatus is to pass this solution to an extractive distillation column or, so-called, recovery column having a side-draw preferably located in the lower half of the recovery column such as, for example, the column disclosed in U.S. Pat. No. 3,399,120. A process stream taken from the side-draw is sent to a much smaller stripping column, for example, having about 10 to about 20 trays. Acetonitrile is concentrated in the overhead vapor draw while the liquid bottoms is returned to the recovery column. The bottoms of this modified recovery column is similar to the bottoms stream issuing from the larger stripper as discussed above.

In the process of this invention, a liquid side-draw is removed from the absorber apparatus, preferably an absorber column or wash column, and at least part and preferably all of the side-draw is directed to a recovery column, preferably to the upper portion of the recovery column, and preferably at a location on the recovery column above where the aqueous solution from the absorber apparatus enters the recovery column. This side-draw is preferably taken in a manner such that it comprises mostly water and minor amounts of acetonitrile. Preferably the absorber apparatus, such as an absorber column, is operated in such a way and the side-draw located in such a manner that the side-draw stream comprises mostly water and minor amounts of acetonitrile. For example, this side-draw stream may comprise about 70 to about 95 weight percent water, more preferably about 85 to about 95 weight percent water. The amount of acetonitrile in the side-draw stream preferably should be less than about 100 parts per million by weight (PPMw), more preferably less than about 50 PPMw acetonitrile, and most preferably less than about 35 PPMw acetonitrile. The side-draw stream may contain other components such as, for example, acrylonitrile and HCN. When the absorber apparatus is an absorber column, the side draw stream is preferably taken from a location on the column in the lower half of the column, more preferably in the lower third of the column. In the process of this invention, this side-draw stream from the absorber apparatus, or at least a part thereof, comprising water is directed to the upper portion of the recovery column, such as the extractive distillation type of recovery column disclosed in U.S. Pat. No. 3,399,120, and can be used to assist in the extractive distillation of acrylonitrile. Preferably, the side-draw stream, or at least a part thereof, is directed to the top tray in a recovery column. In the prior art processes described above, a separate stream of solvent water is added to the top of the recovery column to assist with the extractive distillation of the acrylonitrile. Addition of this extra solvent water exerts an extra load on the recovery column thereby decreasing the processing capacity of the column to distill the acrylonitrile-containing stream. In the method of this invention, the liquid side-draw from the absorber apparatus such as an absorber column preferably provides most or all of the water required for the extractive distillation. The side-draw stream or at least a part thereof from the absorber column is added in place of the solvent water or in place of at least a portion of the solvent water that would be otherwise added to the recovery column. For example, the amount of the side-draw added to the recovery column can be about 10 to about 100 percent, preferably about 50 to about 100 percent, and most preferably about 70 to about 90 percent of the amount of water needed to perform an extractive distillation in the recovery column. This side-draw stream which comprises water used to cause the extractive distillation of the acrylonitrile in the recovery distillation column can reduce the load on the column which would otherwise exist if the full amount of solvent water was added and can also reduce the energy requirements for the distillation in the recovery column. As mentioned above, the amount of acetonitrile in the side-draw stream taken from the absorber apparatus, such as, for example, an absorber column, should be kept to a minimum. One method for obtaining a side-draw stream from an absorber apparatus, such as an absorber column, containing water and low levels of acetonitrile is to cool the absorber apparatus, preferably at a location above the side-draw on the absorber apparatus. Any suitable means for cooling the absorber apparatus can be used. This cooling can be achieved, for example, by placing one or more pump-around coolers in the upper-half section of the absorber apparatus. By pump-around cooler we mean a device that removes a stream from the absorber apparatus, cools the stream, and then returns the stream to the apparatus, for example, at a location lower in the apparatus from where the stream was removed. Preferably at least one pump is used to remove, return, or remove and return the stream. Where the absorber apparatus is a column containing trays, such cooling can be achieved by, for example, removing part or all of the contents of a tray in the column as a stream, cooling the stream, and returning the stream to the column on a tray or trays below the tray from which the stream was taken. Preferably, the amount of cooling used is an amount that will achieve the desired levels of water and acetonitrile in the side-draw stream. The location of where the side-draw stream is taken from the absorber apparatus such as an absorber column is also a factor. This side-draw stream is preferably taken from a location that is about one-third the distance from the bottom of an absorber column to the top of the column. When the absorber column contains trays, the side-draw stream is preferably taken from a location that is about one-third the distance from the bottom tray to the top of the column.

The recovery column is preferably operated in a manner that provides for the separation of acetonitrile from acrylonitrile. Thus, the overhead fraction of the recovery column usually comprises acrylonitrile and hydrogen cyanide (HCN) with low levels of acetonitrile. Preferably the recovery column is operated in a manner such that the amount of acetonitrile in the overhead is less than about 50 PPMw, more preferably less than about 35 PPMw.

Although it is possible to operate the process of this invention without adding any solvent water to the upper portion of the recovery column and using only water from the side-draw stream from the absorber, it is preferable to add some solvent water in addition to the side-draw stream from the absorber apparatus to assist with the extractive distillation.

DESCRIPTION OF THE DRAWING

Referring to the FIGURE, line 10 contains a process stream comprising the reactor effluent gas from the reaction of propylene, ammonia and air in a suitable fluid bed-type reactor containing a suitable fluidized ammoxidation catalyst. The process stream comprises acrylonitrile, HCN, acetonitrile, water vapor and impurities. (The fluid bed-type of reactor is not shown in the FIGURE). The process stream in line 10 is first passed to a quench column 20. In quench column 20, the gaseous process stream is contacted with an aqueous quench liquid from line 22. A bottom stream containing water and impurities is removed from quench column 20 through line 23 and sent to waste treatment.

The cooled reactor effluent gases leave the quench column through line 25 and are sent as feed to partial condenser 30. Any condensed acrylonitrile, acetonitrile and HCN are removed from the partial condenser through line 32 and sent to line 47 before entering the recovery column. The non-condensed material is sent by line 35 as feed to the lower portion of absorber column 40. Wash water enters the upper portion of absorber column 40 at the top through line 42. Non-condensable gases are removed from the absorber column through line 43. An aqueous solution containing water, acrylonitrile, acetonitrile and impurities is removed from the absorber column as a bottoms stream through line 47 and passed to the recovery column (an extractive distillation-type of column) 50.

Absorber column 40 is cooled by pump around coolers 44 and 44a and operated in a manner so that a side-draw stream comprising water, acrylonitrile and HCN with a low amount of, and preferably no, acetonitrile is produced. This side-draw stream is directed to the top portion of recovery column 50 through line 48 to assist with the extractive distillation of feed from line 47. Recovery column 50 is a distillation column having, preferably, about 60 to about 120 trays. Although not shown in the FIGURE, line 48 preferably enters column 50 at the top tray of column 50. Recovery column 50 can be the type of extractive distillation column disclosed in U.S. Pat. No. 3,399,120. In addition to the water from side-draw stream in line 48, water can be added to the top of recovery column 50 through line 53. However, the use of coolers 44 and 44a in absorber column 40 to produce side-draw stream 48 comprising water and minor amounts of acetonitrile, and directing the side-draw stream to the top of extractive distillation column 50, replaces most or all of the solvent water that is ordinarily required for the extractive distillation, thereby greatly reducing the amount of water that would otherwise be necessary for the extractive distillation of acrylonitrile stream 47 in recovery column 50. This reduction in the amount of water required for the extractive distillation increases the hydraulic capacity of column 50, which is beneficial for processing greater amounts of feed 47 in distillation column 50. Acrylonitrile and HCN are removed as an overhead vapor through line 52, condensed in condenser 53 and sent to decanter 54 where an acrylonitrile stream is decanted and sent through line 58 to further purification (not shown). Water from decanter 54 is returned to column 50 through line 56. A bottoms stream containing acetonitrile and water is removed from distillation column 50 through line 51 and may be subjected to additional purification processes such as the process disclosed in U.S. Pat. No. 4,362,603, which is incorporated herein by reference, to isolate purified acetonitrile. Inter-stage pump-around coolers 44 and 44a have a line 59 for withdrawing a stream from a tray in the column, passing the stream through heat exchanger 60 to cool the stream, and returning the cooled stream through line 61 to the column at a tray below the tray from which it was taken. Cooling of the absorber column 40 can also be achieved by removing a portion of the stream in line 47 through line 62, cooling the stream in heat exchanger 63 and returning the cooled stream to the column through line 64.

EXAMPLES

Example 1

Using the apparatus as shown in the FIGURE and simulated using a computer modeling program, an absorber column having 26 theoretical stages was equipped with 28 million BTU/Hr inter-stage cooling in the upper portion of the absorber column. An effluent from the quench column at 99° F. (ca. 37° C.) was treated in the absorber column using a lean water-to-acrylonitrile weight ratio of 9.8. (Lean water is the water feed added to the absorber column 40 through line 42 as shown in the FIGURE.) A liquid side-draw of 89.5 weight percent water, 9 weight percent acrylonitrile, 1.5 weight percent HCN and 25 parts per million by weight (PPMw) acetonitrile was removed from the absorber column through the side-draw and directed to the top of the recovery column as a solvent water replacement. Using the inter-stage cooling and the side-draw stream from the absorber column, all the water for the recovery column came from the side-draw compared to the conventional process with no side-draw from the absorber and only 20 million BTU/Hr inter-stage cooling on the absorber column. In addition to reducing the water circulation rate, 52 percent and 63 percent of the acrylonitrile and HCN, respectively, of the total amounts fed to the absorber column were present in the side-draw stream from the absorber column, which bypassed the conventional route and were directly introduced to the recovery column top section. The resulting increases in the hydraulic capacity of the absorber and recovery columns were 25 percent and 27 percent, respectively.

Example 2

Using the process of this invention, a computer simulation was performed to process increased product throughput using fixed column sizes and hardware. An absorber column having 26 theoretical stages was equipped with 40 million BTU/Hr inter-stage cooling in the upper portion of the absorber. Reactor effluent from the quench column at 99° F. (ca 37° C.) was increased by 50 percent and was introduced to the absorber column using a lean water-to-acrylonitrile weight ratio of 9.1. A liquid side-draw of 89.4 weight percent water, 9 weight percent acrylonitrile, 1.6 weight percent HCN and 30 per million by weight (PPMw) acetonitrile was removed from the absorber column side-draw and directed to the top of the recovery column as a solvent water replacement. About 47 percent of the acrylonitrile and 62 percent of HCN of the total amounts of acrylonitrile and HCN fed to the absorber column were present in the side-draw stream and, therefore, were directly introduced into the recovery column top section. Consequently, and advantageously, those amounts of acrylonitrile and HCN bypassed the conventional recovery and purification route.

These examples show that, compared to a conventional absorber-recovery process, extra cooling in the absorber column, and removing an aqueous, side-draw stream from the absorber column and adding it to the recovery column to effect the extractive distillation of the feed to the recovery column, resulted in increasing the hydraulic capacity of both the absorber and recovery columns, along with a reduction in solvent water circulation rate. By the use of this invention, an additional product throughput, for example, fifty percent more product throughput, can be achieved for a given sized distillation column, such as a recovery column.

Only certain embodiments and examples of the invention have been set forth and alternative embodiments and various modifications will be apparent from the above description to those skilled in the art. These and other alternatives are considered equivalents and within the spirit and scope of the invention.

U.S. Provisional Patent Application 60/535,414 filed on Jan. 9, 2004 is incorporated herein by reference in its entirety.

That which is claimed is:

1. A process for the recovery and purification of olefinically unsaturated nitrites from a process stream comprising:
   (a) contacting a process stream comprising olefinically unsaturated nitrile with an aqueous quench liquid in a quench apparatus to produce a gaseous quench effluent comprising olefinically unsaturated nitrile;
   (b) contacting the gaseous quench effluent with a liquid comprising water in an absorber apparatus to form an aqueous mixture comprising absorbed olefinically unsaturated nitrile;
   (c) withdrawing from the absorber apparatus a side-draw stream comprising water and a stream comprising olefinically unsaturated nitrile;
   (d) introducing the stream comprising olefinically unsaturated nitrile to a first distillation column where the stream comprising olefinically unsaturated nitrile is distilled in an extractive distillation to form a fraction comprising olefinically unsaturated nitrile, and
   (e) directing the side-draw stream comprising water to the first distillation column for the extractive distillation of the olefinically unsaturated nitrile in the first distillation column.

2. The process of claim 1 wherein the olefinically unsaturated nitrile comprises acrylonitrile.

3. The process of claim 2 wherein the process stream is obtained by the ammoxidation of a feedstock comprising propylene.

4. The process of claim 1 wherein the absorber apparatus is an absorber column.

5. The process of claim 1 wherein the stream comprising olefinically unsaturated nitrile withdrawn from the absorber column is a bottoms stream and wherein the side-draw stream enters the first distillation column at a location above where the bottoms stream enters the first distillation column.

6. The process of claim 4 wherein the absorber column is cooled.

7. The process of claim 6 wherein at least one pump around cooler is used for cooling the absorber column.

8. The process of claim 1 wherein the side-draw stream comprises at least about 70 percent water by weight.

9. The process of claim 8 wherein the side-draw stream comprises less than about 100 PPMw acetonitrile.

10. An energy efficient process for the recovery and purification of acrylonitrile from a process stream produced by the ammoxidation of a propylene, propane or mixtures thereof comprising:
   (a) contacting the process stream comprising acrylonitrile with an aqueous quench liquid in a quench apparatus to produce a gaseous quench effluent comprising acrylonitrile;
   (b) contacting the gaseous quench effluent with a liquid comprising water in an absorber column to form an aqueous mixture comprising absorbed acrylonitrile;
   (c) withdrawing from the absorber column a side-draw stream comprising water and a bottoms stream comprising acrylonitrile;
   (d) introducing the bottoms stream to a first distillation column where the bottoms stream is distilled in an extractive distillation to form a top fraction comprising acrylonitrile, and
   (e) directing the side-draw stream comprising water to the first distillation column for the extractive distillation of the acrylonitrile in the first distillation column.

11. The process of claim 10 wherein the absorber column is cooled.

12. The process of claim 11 wherein at least one pump-around cooler is used for cooling.

13. The process of claim 10 wherein the side-draw comprises at least about 70 weight percent water.

14. The process of claim 13 wherein the side-draw comprises less than about 100 PPMw acetonitrile.

15. The process of claim 10 wherein solvent water is also added to a top portion of the first distillation column to assist with the extractive distillation.

16. The process of claim 10 wherein the side-draw is taken from the lower half of the absorber column.

* * * * *